(12) United States Patent
Hu et al.

(10) Patent No.: US 9,804,122 B2
(45) Date of Patent: Oct. 31, 2017

(54) EMBEDDED NOBLE METAL ELECTRODES IN MICROFLUIDICS

(71) Applicants: International Business Machines Corporation, Armonk, NY (US); BIONANO GENOMICS, INC., San Diego, CA (US)

(72) Inventors: Huan Hu, Yorktown Heights, NY (US); Michael F. Lofaro, Brookfield, CT (US); Joshua T. Smith, Croton on Hudson, NY (US); Daniel J. Solis, Escondido, CA (US); Benjamin H. Wunsch, Mt. Kisco, NY (US)

(73) Assignees: INTERNATIONAL BUSINESS MACHINES CORPORATION, Armonk, NY (US); BIONANO GENOMICS, INC., San Diego, CA (US)

( * ) Notice: Subject to any disclaimer, the term of this patent is extended or adjusted under 35 U.S.C. 154(b) by 60 days.

(21) Appl. No.: 14/952,161

(22) Filed: Nov. 25, 2015

(65) Prior Publication Data

US 2017/0120246 A1 May 4, 2017

Related U.S. Application Data

(63) Continuation of application No. 14/928,596, filed on Oct. 30, 2015.

(51) Int. Cl.
*H01B 13/00* (2006.01)
*B23P 15/00* (2006.01)
(Continued)

(52) U.S. Cl.
CPC .. *G01N 27/44791* (2013.01); *B01L 3/502707* (2013.01); *B01L 2200/10* (2013.01);
(Continued)

(58) Field of Classification Search
CPC ............... H01L 21/3212; H01L 21/32139
(Continued)

(56) References Cited

U.S. PATENT DOCUMENTS

| 6,174,812 B1 * | 1/2001 | Hsiung et al. ........ H01L 21/288 |
| | | 257/E21.174 |
| 6,238,592 B1 * | 5/2001 | Hardy et al. ............. C09G 1/02 |
| | | 252/79.1 |

(Continued)

OTHER PUBLICATIONS

Huan Hu,"Embedded Noble Metal Electrodes in Microfluidics", U.S. Appl. No. 14/928,596, filed Oct. 30, 2015.
(Continued)

*Primary Examiner* — Thomas Pham
(74) *Attorney, Agent, or Firm* — Cantor Colburn LLP; Vazken Alexanian

(57) ABSTRACT

A technique relates to manufacturing a nanogap. An oxide layer is disposed on top of a substrate. A release layer is disposed in a pattern on top of the oxide layer. A patterned trench is etched into the oxide layer using the pattern of the release layer. A metal layer is disposed on the release layer and in the patterned trench. A polish removes the release layer, thereby removing both the release layer and a portion of the metal layer having been disposed on top of the release layer, such that the metal layer remaining includes a first metal part and a second metal part connected by a metal nanowire. The metal layer remaining is coplanar with the oxide layer. A nanochannel is formed in the oxide layer in a region of the metal nanowire. The nanogap is formed in the metal nanowire separating the first and second metal parts.

12 Claims, 9 Drawing Sheets

(51) Int. Cl.
*C03C 25/00* (2006.01)
*C23F 1/00* (2006.01)
*G01N 27/447* (2006.01)
*B01L 3/00* (2006.01)

(52) U.S. Cl.
CPC ....... *B01L 2200/12* (2013.01); *B01L 2300/06* (2013.01); *B01L 2300/0887* (2013.01); *B01L 2300/0896* (2013.01); *B01L 2400/0421* (2013.01)

(58) Field of Classification Search
USPC .......................................................... 216/17
See application file for complete search history.

(56) References Cited

U.S. PATENT DOCUMENTS

| | | | | |
|---|---|---|---|---|
| 2002/0079552 A1* | 6/2002 | Koike | ................ | H01L 23/5258 257/529 |
| 2003/0040172 A1* | 2/2003 | Brennan | ........... | H01L 21/31144 438/622 |
| 2007/0199927 A1* | 8/2007 | Gu et al. | ................ | B23K 26/04 219/121.69 |

OTHER PUBLICATIONS

List of IBM Patents or Patent Applications Treated as Related; Dated Filed: Feb. 10, 2016, p. 1-2.

* cited by examiner

EMBEDDED NOBLE METAL ELECTRODES IN MICROFLUIDICS

DOMESTIC PRIORITY

This application is a continuation of U.S. patent application Ser. No. 14/928,596, filed Oct. 30, 2015, the disclosure of which is incorporated by reference herein in its entirety.

BACKGROUND

The present invention relates to nanofluidic chips, and more specifically, to embedded metal electrodes (e.g., noble metals) for on-chip detection and/or manipulation of biological material in microfluidics.

Nanofluidics is the study of the behavior, manipulation, and control of fluids that are confined to structures of nanometer (typically 1-100 nanometers (nm)) characteristic dimensions. Fluids confined in these nanometer structures exhibit physical behaviors not observed in larger structures, such as those of micrometer dimensions and above, because the characteristic physical scaling lengths of the fluid (e.g., Debye length, hydrodynamic radius) very closely coincide with the dimensions of the nanostructure itself. In nanofluidics, fluids are moved, mixed, separated, or otherwise processed. Numerous applications employ passive fluid control techniques like capillary forces. In some applications external actuation means are additionally used for a directed transport of the fluids.

SUMMARY

According to one embodiment, a method of manufacturing a nanogap is provided. The method includes disposing an oxide layer on top of a substrate, disposing a release layer in a pattern on top of the oxide layer, etching a patterned trench into the oxide layer using the pattern of the release layer, and disposing a metal layer on the release layer and in the patterned trench, such that the metal layer is disposed on top of the oxide layer in the patterned trench. Also, the method includes performing a polish to remove the release layer, thereby removing both the release layer and a portion of the metal layer having been disposed on top of the release layer, such that the metal layer remaining includes a first metal part and a second metal part connected by a metal nanowire. The metal layer remaining is coplanar with the oxide layer. Further, the method includes forming a nanochannel in the oxide layer in a region of the metal nanowire, and forming the nanogap in the metal nanowire, such that the first metal part and the second metal part are separated by the nanogap.

According to one embodiment, a structure formed with a nanogap is provided. The structure includes an oxide layer on top of a substrate, a patterned trench formed into the oxide layer according to a pattern of a sacrificial release layer to be removed, and a metal layer formed in the patterned trench of the oxide layer. The metal layer remains after removal of the sacrificial release layer, where the metal layer is coplanar with the oxide layer, and where the metal layer in the patterned trench includes a first metal part, a second metal part, and a metal nanowire between the first and second metal parts. The nanogap formed in the metal nanowire, such that the first metal part and the second metal part are separated by the nanogap. A nanochannel is formed in the oxide layer in a region of the nanogap.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

DETAILED DESCRIPTION

Figure 1:
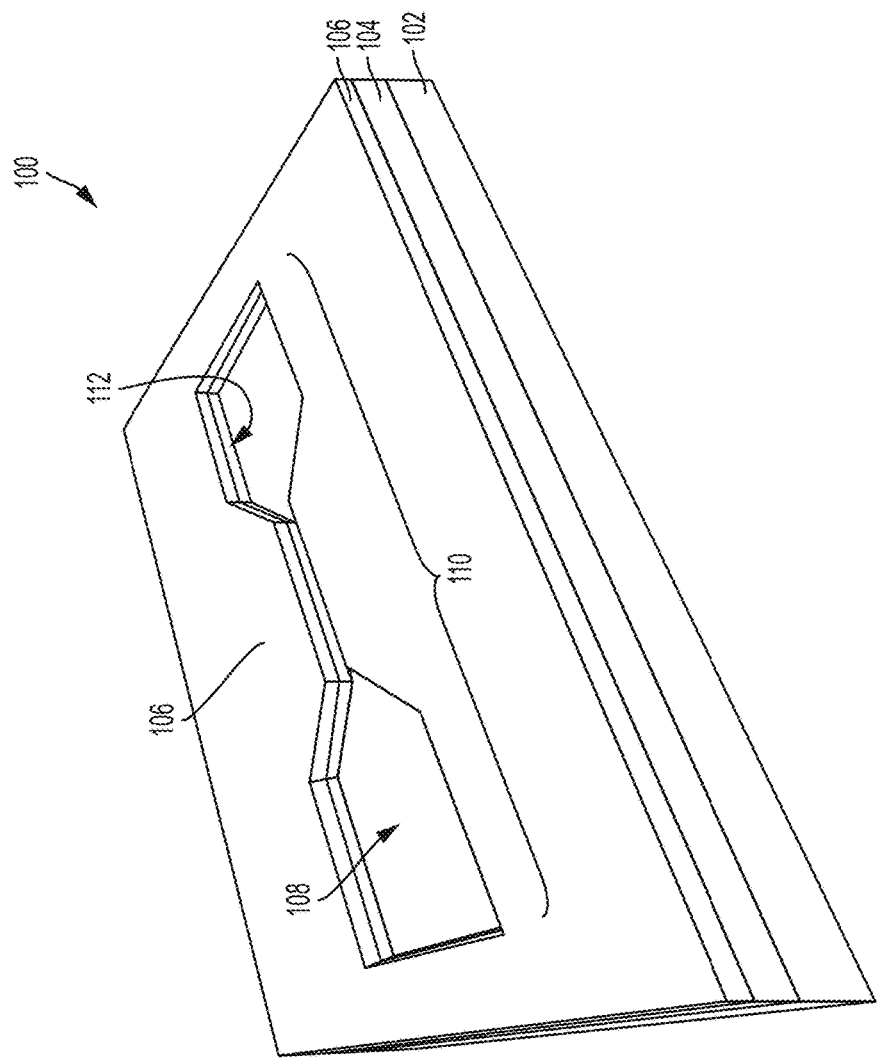
FIG. 1 is a schematic of a perspective view of an intermediate structure according to an embodiment.

Embodiments provide a technique of integrating embedded metal electrodes (such as, e.g., noble metal electrodes that are utilized for reliable sensing and manipulation of biological material in microfluidics) on a silicon-based microfluidic chip platform by highly scalable and manufacturable means. The use of noble metals is utilized to avoid irreversible modification processes, such as oxidation, of the electrodes as they interface with the microfluidic environment. Because these electrodes can be embedded in an oxide material to make them coplanar with the oxide surface rather than sitting on the surface of the chip, a number of bonding schemes can be implemented to hermetically seal them along with accompanying microfluidic/nanofluidic features. One or more embodiments demonstrate electrodes fabricated at dimensions down to approximately 20 nanometers (width and thickness) providing a path for high-density integration.

On-chip electrodes can be incorporated into lab-on-a-chip (LOC) or micro-total analysis systems (µTAS) to perform several functions, such as sorting of net charged biological material, electrokinetic driving of the same to induce flow in a specific direction, or for sensing biomolecules by transducing events into electrical signals when the electrodes are configured in a nanogap arrangement.

Sensing. Of the so-called planar nanogap devices demonstrated in the state-of-the-art, perhaps one of the most promising is a state-of-the-art device from Princeton University, which showed label-free DNA detection. However, despite a positive demonstration of detection, this state-of-the art device involves a complicated, low-yield processing scheme with (1) electrodes sitting on top of a substrate, making it difficult to seal the nanochannels, and (2) multiple angled e-beam depositions to coat the sidewalls of the nanochannels with metal and to form the top electrodes, resulting in difficult-to-control gap sizes. Variability in the gap size, in turn, leads to unreliable detection of biomolecules. Multiple angled deposition processes also have the added problems of lower throughput, stringent wafer alignment requirements during deposition(s), and variable metal thickness along the electrodes.

Another state-of-the-art device may have nanogap size down to 2 nm using a helium (He) ion beam to cut a palladium (Pd) nanowire into a set of nanogap electrodes. However, the Pd electrodes in this case lay on top of a substrate without a nanochannel hence there is no controllable means of inducing molecules to pass between the electrodes through the nanogap.

In the context of DNA tunneling recognition, recent work has emerged for vertical nanogaps in which electrodes are fabricated in a layered tunnel junction configuration. This configuration also suffers from lack of ability to control the velocity of the molecules passing by the gap.

Separation by charge. Electrophoresis is a primary source for separating entities by charge in microfluidic chips, the driving force of which is the electric field. The electric field can be applied via contacting a set of electrodes with the fluid contained on the LOC device. In many of these state-of-the art configurations, large bulk electrodes external to the chip are used to drive this process, requiring larger voltages than would be needed with localized, scaled electrodes integrated on chip.

Control over fluid flow. Using electrohydrodynamics principles, shaped electrostatic fields can be used to create a hydrostatic pressure (or motion) in fluids to induce flow in a particular direction. As an alternative to first generation microfluidic biochips that contained micropumps, microvalues, and microchannels to drive fluid, digital microfluidics approaches have been explored more recently, where discrete droplets of sample or reagent are manipulated on a grid of droplet-sized electrodes. At this point in time, such control has been limited to droplet-based microfluidics.

However, if highly-scaled electrodes could be co-integrated with microfluidic features, then a higher level of control over the direction and velocity of fluid flow can be exerted locally throughout the chip using smaller voltages, providing a means of high-precision fluidic control. Accordingly, embodiments provide highly-scaled electrodes. In accordance with embodiments, by having localized electrodes that are much closer together allows a certain (i.e., predefined) electric field strength to be maintained with less charge. Very simply the electric field strength between two charges is $E=kQ/d^2$ where d is the distance between charges, k is Coulomb's constant, and Q is the magnitude of the charge. Having a series of electrodes along a microfluidic channel each at a different potential would allow localized velocity control in each region since each region would have a different field strength driving the fluidics.

Additionally, creating electrodes that can interface with microfluidics to sense or manipulate material contained within the fluid may be considered a unique challenge. The state-of-the-art work illustrates this challenge well, and shows fundamentally that it is possible to detect biomolecules (DNA in their case). However, in the state-of-the-art, their chip requires external probes that prohibit densely packed arrays and requires a complicated, low-yield fabrication scheme with the bulk of the electrodes out-of-plane from the substrate; having electrodes out-of-plane with the substrate makes it difficult to seal the nanochannels.

According to embodiments, one or more techniques of fabricating noble metal electrodes embedded within a substrate provide a more ideal or useable structure, whereby manufacturable bonding schemes are possible along with high-yield to reduce cost and enable redundant measurements. It should be appreciated that accomplishing this task, particularly for very thin metals (tens of nanometers and below), is nontrivial, as can be recognized in embodiments.

Now turning to the figures, FIGS. 1-6 illustrate fabrication processes of fabricating embedded metal electrodes. It should be appreciated that, although fabrication processes are discussed for fabricating a single metal electrode and nanogap, numerous embedded metal electrodes may be simultaneously formed along the nanochannel or in many nanochannels fabricated in parallel on the same chip.

FIG. 1 is a schematic of a perspective view of an intermediate structure 100 according to an embodiment. FIG. 1 illustrates electrode trench definition.

In FIG. 1, an oxide layer 104 is grown or deposited on top of a substrate 102. The substrate 102 may be a wafer, such as a silicon wafer, germanium wafer, etc. The substrate 102 should have a high resistance, i.e., have few dopants (such as an intrinsic or unintentionally doped silicon wafer with ultra low impurity concentration, because doped silicon contributes to conductivity).

The oxide layer 104 should be relatively thick (for electrode isolation). In one implementation, the oxide layer 104 may have a thickness of about 300 nm in the z-axes. In another implementation, the thickness of the oxide layer 104 may be about 300-2000 nm. In one case, the oxide layer 104 may be silicon dioxide ($SiO_2$). Other oxide materials may be utilized.

A release layer 106 is deposited on the top surface of the structure 100, such that the release layer 106 is on top of the oxide layer 104. The release layer 104 may be a resist material designed to be exposed and developed into a desired pattern using photolithography, as understood by one skilled in the art. Also, the release layer 106 may be defined using e-beam lithography or other form of lithography, e.g. imprint lithography, as understood by one skilled in the art.

An electrode pattern 110 may be defined with lithography in the release layer 106. The electrode pattern 110 is formed in the desired shape of metal electrodes (including a nanowire).

The electrode pattern 110 in the release layer 106 may be used as a mask to transfer the same pattern as a trench 108 down into the oxide layer 104 using etch processes. In one implementation, the patterned trench 108 may be about 20 nm deep (in the z-axes) in the oxide layer 104, such that the metal electrode can correspondingly be 20 nm deep. In another implementation, the depth of the trench may be about 20-100 nm, and accordingly the metal electrode is correspondingly about 20-100 nm thick. In one case, reactive-ion etching (RIE) may be used to etch the trench 108 and form anisotropic trench walls 112 of the oxide layer 104 without undercutting the release layer 106 (e.g., resist layer).

Figure 2:
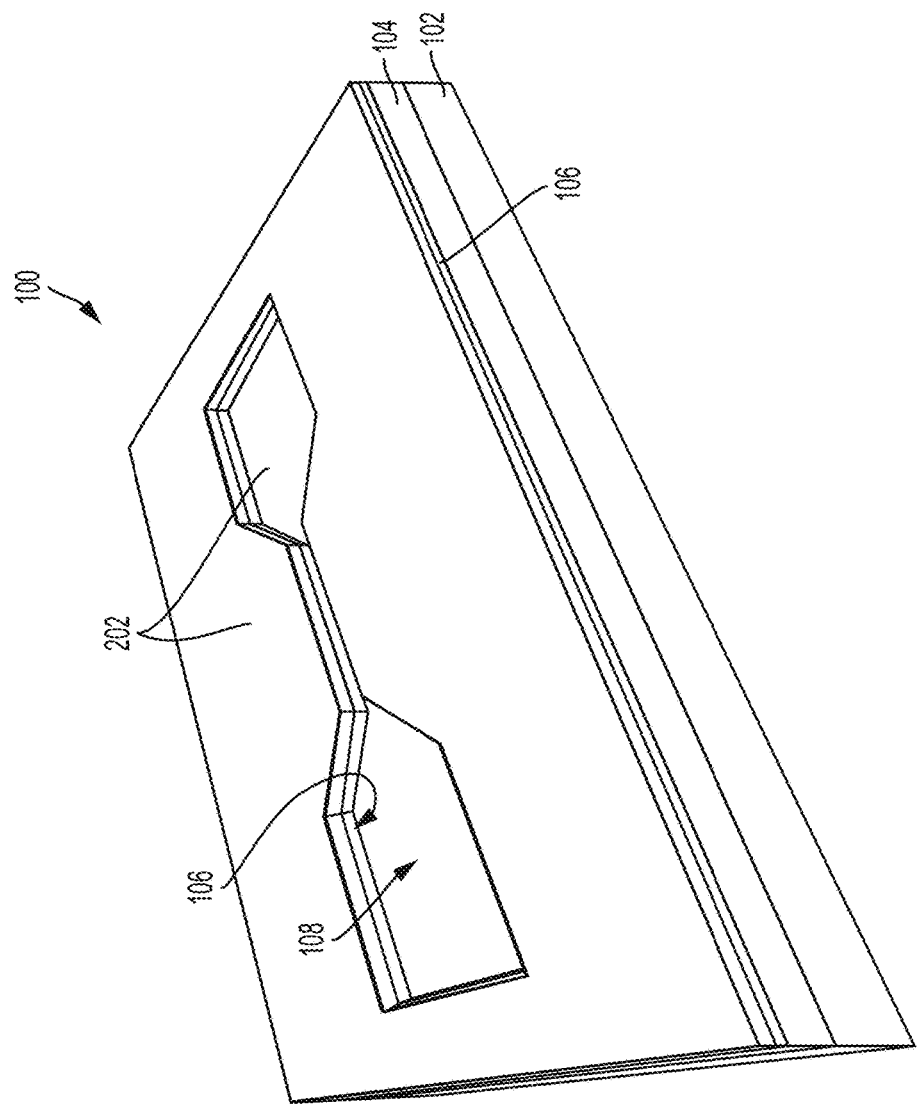
FIG. 2 is a schematic of a perspective view of the intermediate structure illustrating metal deposition according to an embodiment.

FIG. 2 is a schematic of a perspective view of the intermediate structure 100 illustrating metal deposition according to an embodiment. As seen in FIG. 2, a metal layer 202 is deposited on top of the release layer 106 and in the patterned trench 108 (according to the electrode pattern 110). The deposition of the metal layer 202 is controlled to fill the trench 108 in the oxide layer 104. Accordingly, if a 20 nm trench 108 is etched into the oxide layer 104, then a 20 nm metal layer 202 is deposited on top of the intermediate structure 100. The metal of the metal layer 202 may be a noble metal such as palladium, platinum, and/or gold with an appropriate adhesion layer such as titanium or chromium, as required.

In one implementation, metal evaporation may be utilized to deposit the metal layer 202 on top of the intermediate structure 100, and the metal evaporation method may use e-beam evaporation to fill trench 108 with metal until the metal layer 202 filling the trenches 108 is coplanar with the oxide surface of the oxide layer 104. In other words, the metal layer 202 is to be level with the top surface of the oxide layer 104. In one implementation, the oxide trench 108 etch depth may be evaluated for a given process, with a monitor wafer for example, and subsequently a well-calibrated metal evaporation tool can easily deposit a metal layer with angstrom-level accuracy and its thickness measured real time with a quartz crystal monitor. The sacrificial release layer 106 (e.g., sacrificial resist layer) is to serve as a release layer during polishing.

Figure 3:
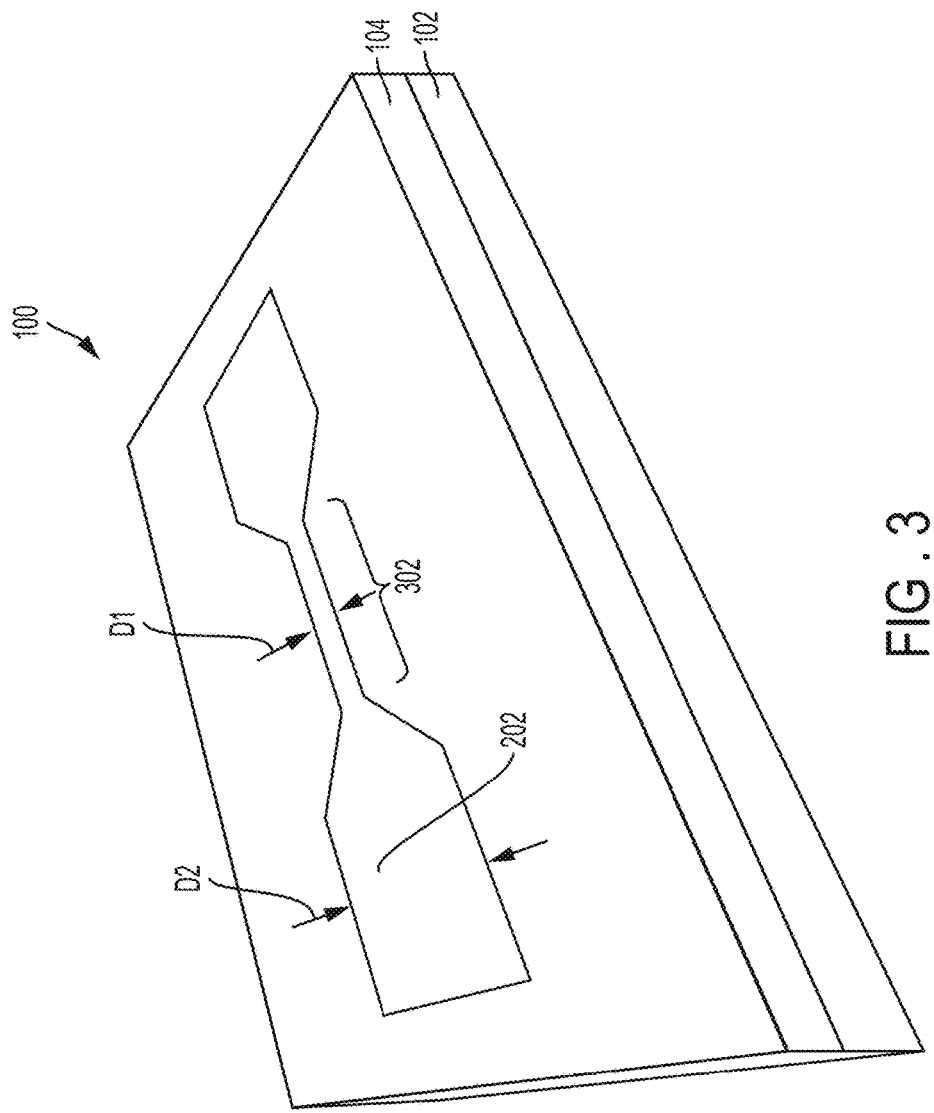
FIG. 3 is a schematic of a perspective view of the intermediate structure illustrating planarization/polishing according to an embodiment.
Figure 3:
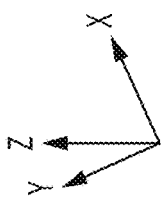

FIG. 3 is a schematic of a perspective view of the intermediate structure 100 illustrating planarization/polishing according to an embodiment.

Planarization/polishing (e.g., chemical mechanical polishing (CMP)) may be performed using a water polish with appropriate down force to selectively remove the release layer 106 (e.g., resist layer) and unwanted metal 202 on top of the release layer 106 while keeping the metal electrodes of the metal layer 202 intact within the trenches 108. Also, embedding the metal layer 202 in the oxide 104 together with the down force of the polish process reduces fencing and causes no dishing due to the absence of CMP chemistry and slurry particles. More regarding the water polish is discussed below.

Figure 4:
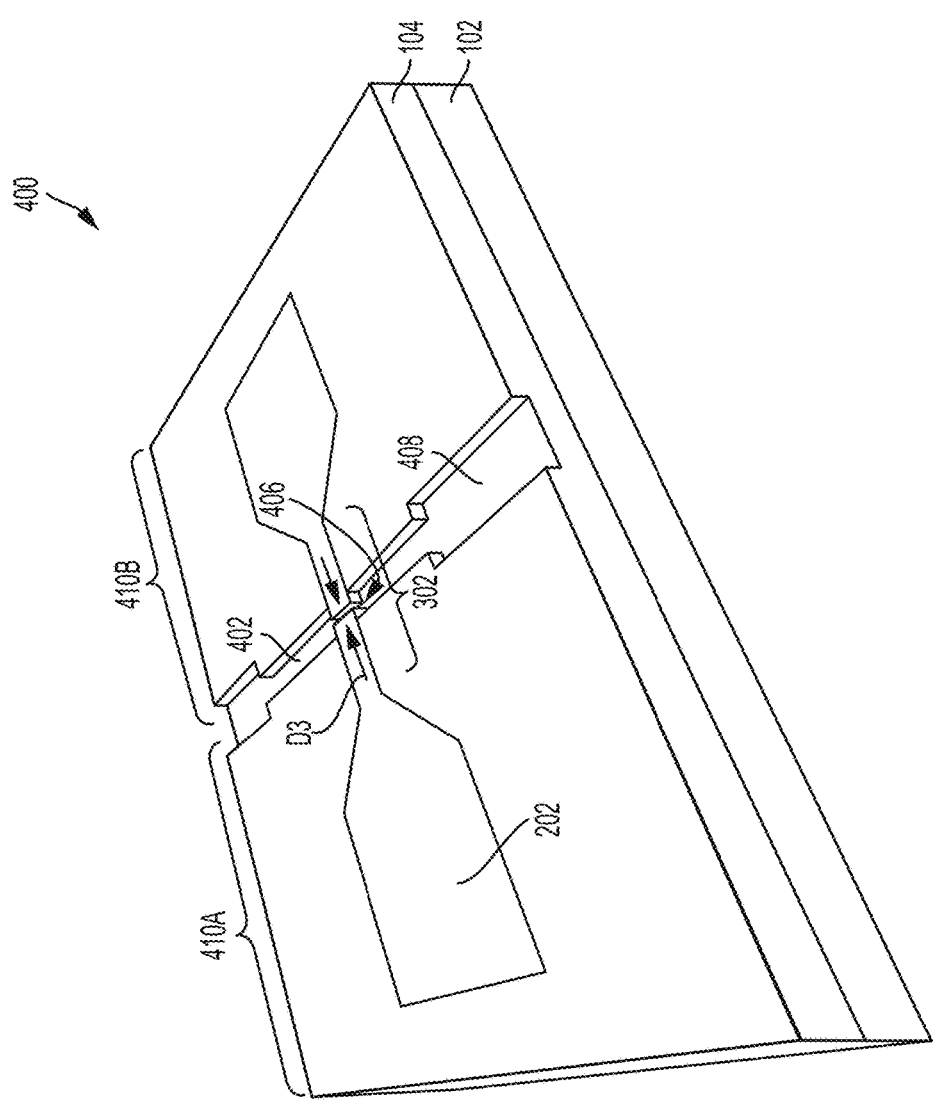
FIG. 4 is a schematic of a perspective view of a structure illustrating the completed embedded metal electrodes in a nanochannel according to an embodiment.

In FIG. 3, a metal nanowire 302 is shown connecting two metal pads of the metal layer 202. The metal nanowire 302 is cut to form a nanogap as shown in FIG. 4. It should be noted that the metal nanowire 302 is cut after the nanochannel is formed, which helps to avoid alignment issues. The width in the y-axis of the metal nanowire 302 is distance D1. In one implementation, the distance D1 of the metal nanowire 302 may be about 10-100 nm.

The metal pads (in rectangle shapes with fanouts extending from the metal nanowire 302) are on opposite sides of the metal nanowire 302. The width (e.g., distance D2) in the y-axis of the metal pads may be about 200-2000 nm.

As an additional/optional fabrication process, a thin coating of another oxide layer (not shown) may be conformally deposited on top of the intermediate structure 100 in FIG. 3. This thin coating of the other oxide layer may be about 10 nm thick in one implementation. In another implementation, the thin coating of the other oxide layer may range from about 5-50 nm. The thin coating of the other oxide (e.g., silicon dioxide) may be applied by plasma-enhanced chemical vapor deposition (PECVD). In one case, there may be a small gap around the perimeter or a portion of the perimeter of the metal layer 202 in the trench 108 (i.e., along the sidewalls of the metal such as between the metal 202 and the oxide layer 104). The thin coating of the other oxide serves the purpose of filling this small gap around the sides of the metal layer 202 to avoid wetting when microfluidics are introduced, and the entire top surface of the intermediate structure remains level after the conformal coating of the other oxide on the metal layer 202 and oxide layer 104. Furthermore, by depositing the thin coating of the other oxide on the top surface of the intermediate structure 100 in FIG. 3, the thin coating creates a better bonding material/surface for the cover slip that is applied below to seal the nanochannel 408 of FIG. 4.

FIG. 4 is a schematic of a perspective view of a structure 400 illustrating the completed embedded metal electrodes according to an embodiment. In FIG. 4, a nanochannel 402 may be etched in the oxide layer 104 on opposite sides of the metal nanowire 302. Opposing ends of the nanochannel 402 may be etched to have a wider channel portion 408 that feeds into the narrower nanochannel. The nanochannel 402 including the wider channel 408 may be etched using RIE etching, to be perpendicularly aligned to the nanowire 302.

A nanogap 406 of desired width D3 may be cut into the metal nanowire 302. The nanogap 406 is cut to be substantially parallel to the nanochannel 402. Various techniques may be utilized to cut the nanogap 406, including helium (He) ion beam, focused ion beam, etc.

The nanogap 406 separates the metal layer 202 into two embedded metal electrodes 410A and 410B, such that each electrode 410A and 410B has its own metal pad (i.e., rectangular shape with a triangular end) and a portion of the nanowire 302 (which is now split in two).

Figure 5:
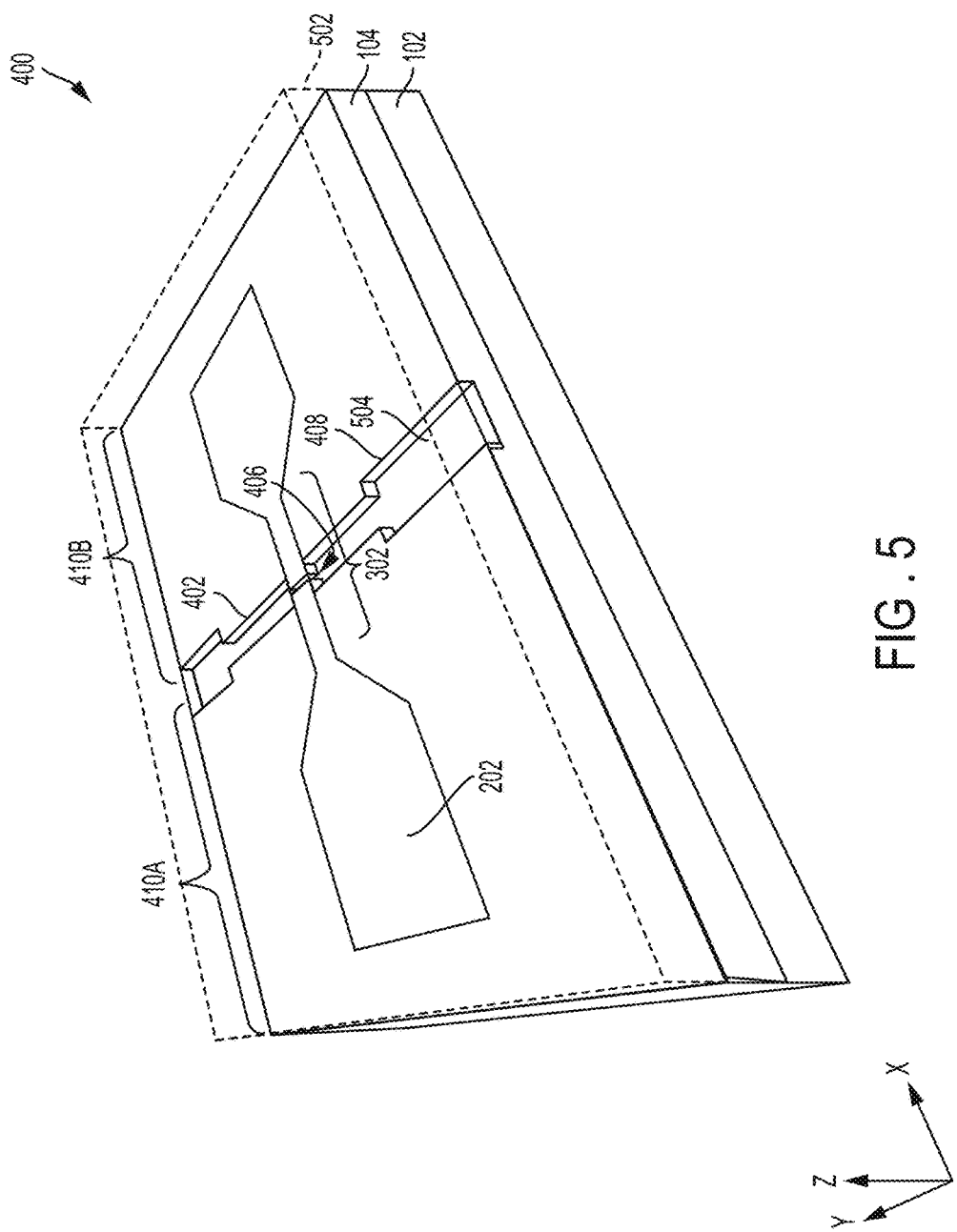
FIG. 5 is a schematic of a perspective view of the structure illustrating an example of sealing nanochannels according to an embodiment.

FIG. 5 is a schematic of a perspective view of the structure 400 illustrating an example of sealing the nanochannels 402 according to an embodiment. A cover slip 502 may be formed on top of the structure 400 or at least on top of the nanochannels 402 and nanogap 406. The cover slip 502 is a covering that stops fluid 504 from leaking out of the nanochannels 402 (including the wider nanochannel portions 408) and the nanogap 406.

In FIG. 5, the cover slip 502 is shown as being transparent for explanation purposes. However, it should be appreciated that the cover slip 502 is not required to be transparent. In one implementation, the cover slip 502 may be about 100 microns (μm) thick in the z-axis. In another implementation, the cover slip 502 may have a thickness that ranges from about 1-500 μm.

The cover slip 502 should be a material having enough rigidness so as not to fill the nanochannel 402 and the nanogap 406. Examples of the cover slip 502 may include glass, polydimethylsiloxane (PDMS), etc., which are bonded to the top surface of the structure 400 (i.e., bonded to the coplanar top surfaces of the metal electrodes 410A, 410B and oxide layer 104). Additionally, the cover slip 502 may be a thin layer of oxide applied by wafer-to-wafer bonding, as understood by one skilled in the art.

Figure 6:
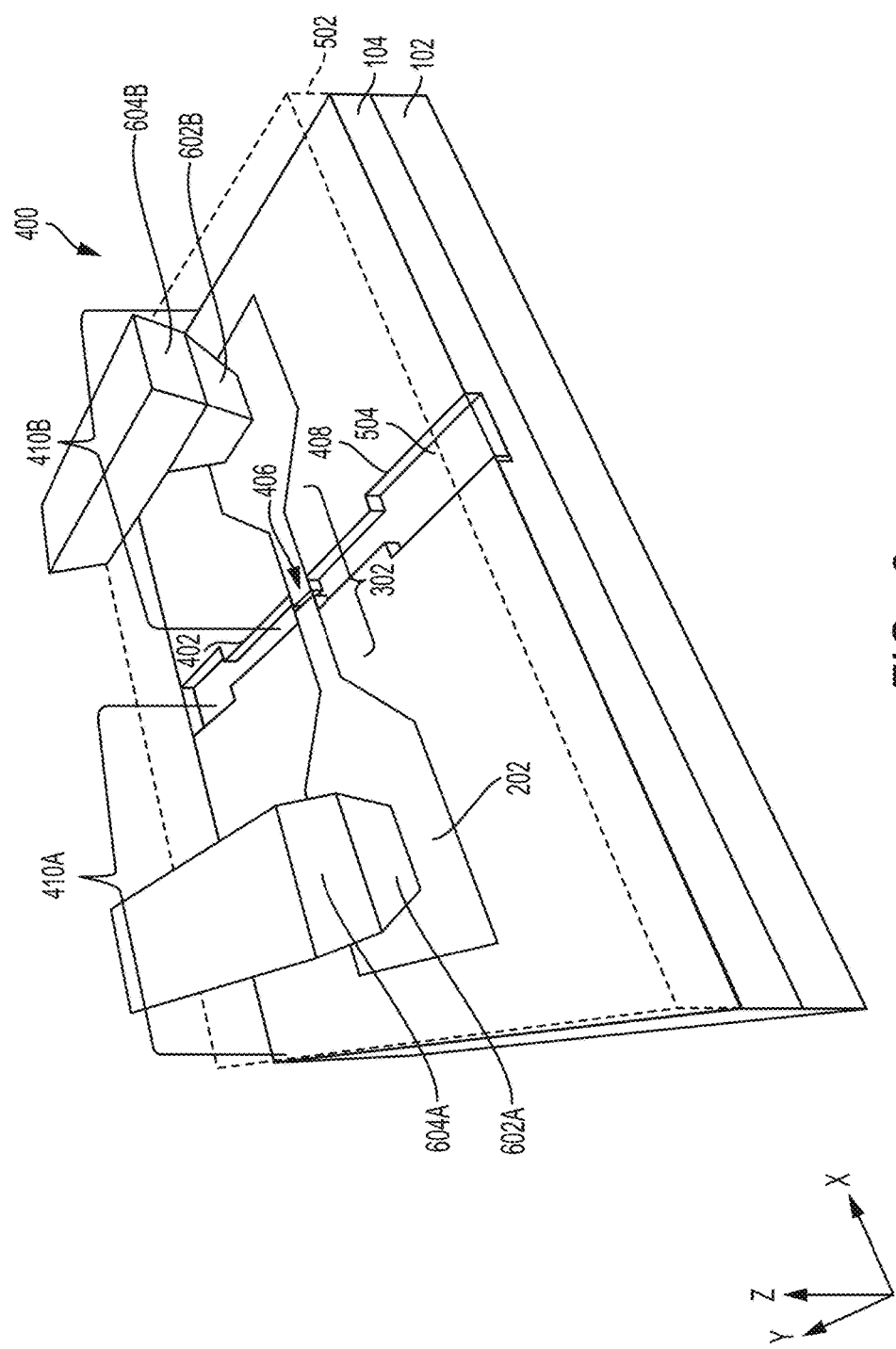
FIG. 6 is a schematic of a perspective view of the structure illustrating back-end-of-the-line (BEOL) processing according to an embodiment.

FIG. 6 is a schematic of a perspective view of the structure 400 illustrating back-end-of-the-line (BEOL) processing according to an embodiment. In FIG. 6, holes reaching down to the individual metal pads of the embedded metal electrodes 410A and 410B may be formed through the cover slip 502. The holes may be filled with a conductive material to form plugs or vias 602A and 602B respectively connected to the metal electrodes 410A and 410B. Example materials used for the plugs or vias 602A, 602B may include tungsten, copper, titanium, titanium nitride, tantalum, tantalum nitride, etc., such that a suitable ohmic contact if formed.

Interconnects 604A and 604B may be respectively connected to the tops of the plugs or vias 602A and 602B.

Figure 7:
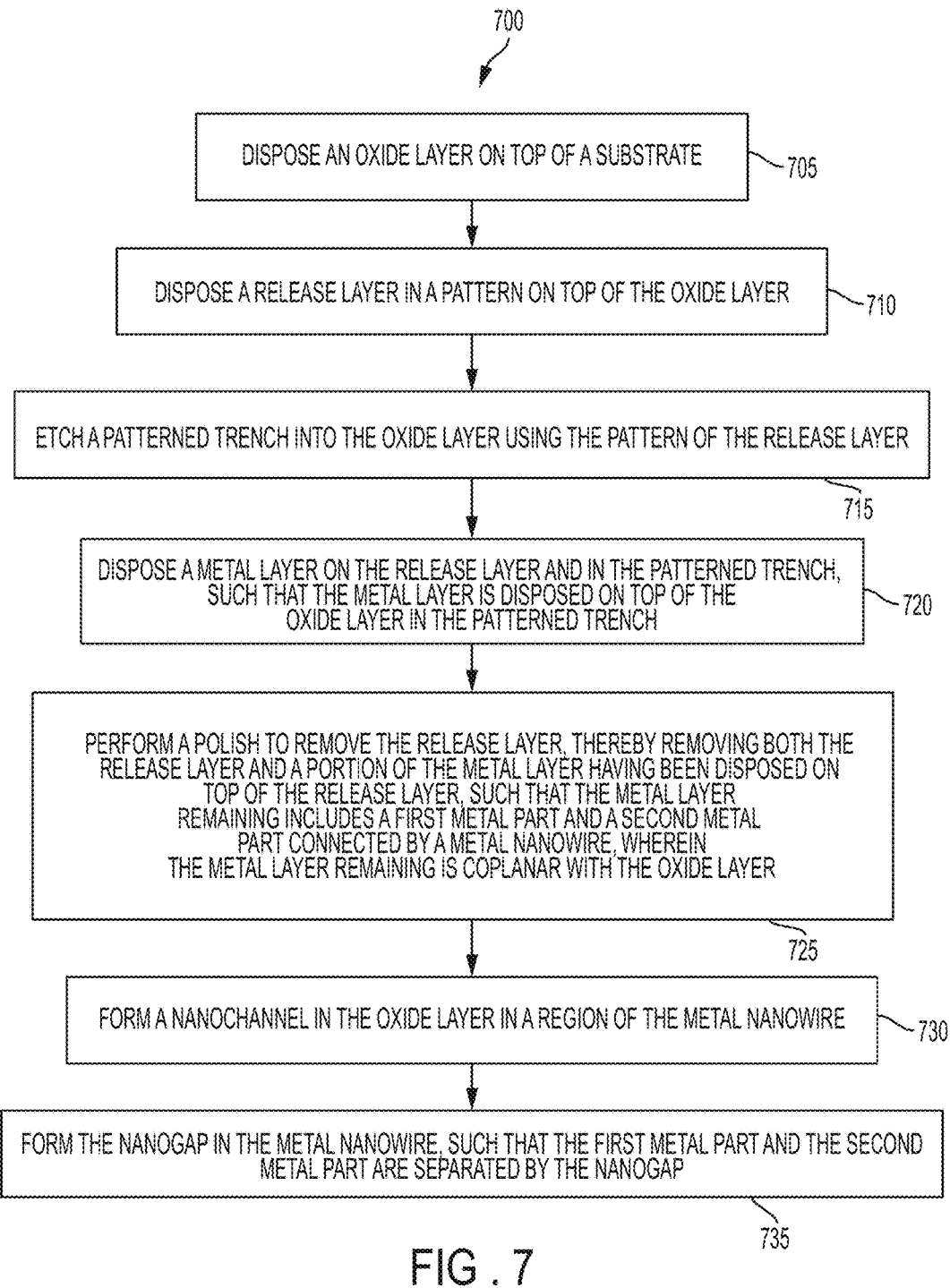
FIG. 7 is a flow chart of a method of manufacturing embedded metal electrodes having a nanowire with a nanogap according to an embodiment.

FIG. 7 is a flow chart 700 of a method of manufacturing embedded metal electrodes and a nanowire with a nanogap according to an embodiment.

At block 705, the oxide layer 104 is disposed on top of the substrate 102.

At block 710, the (sacrificial) release layer 106 is disposed in an electrode pattern 110 on top of the oxide layer 104 as depicted in FIG. 1.

At block 715, the patterned trench 108 is etched into the oxide layer 104 using the pattern 110 of the release layer 106, as depicted in FIG. 1.

At block 720, the metal layer 202 is disposed on top of the release layer 106 and in the patterned trench 108, such that the metal layer 202 is disposed on top of the oxide layer 104 in the patterned trench 108, as depicted in FIG. 2.

At block 725, a polish is performed to remove the release layer 106, thereby removing both the release layer 106 and a portion of the metal layer 202 having been disposed on top of the release layer 106, such that the metal layer 202 remaining includes a first metal part and a second metal part connected by a metal nanowire 302, where the metal layer 202 remaining is coplanar with the oxide layer 104, as depicted in FIG. 3. In one case, after performing the polish to remove the release layer, a coating of another oxide layer (not shown) is disposed on top of the metal layer 202 and the oxide layer 104 (e.g., to fill any small gap around the sides of the metal layer 202 thereby avoiding wetting when microfluidics are introduced, and to provide better bonding to the cover 502).

At block 730, the nanochannel 402 is formed in the oxide layer 104 in a region of the metal nanowire 302, as depicted in FIG. 4.

At block 735, the nanogap 406 is formed in the metal nanowire 302, such that the first metal part (e.g., first metal electrode 410A) and the second metal part (e.g., second metal electrode 410B) are separated by the nanogap 406.

A cover 502 may be formed over at least the nanochannel 402, the nanogap 406, and the first and second metal parts (e.g., first and second metal electrodes 410A and 410B). The nanogap 406 may be formed by cutting the metal nanowire 302 (in half) to separate the first metal part and the second metal part.

Performing the polish to remove the release layer 106 comprises performing mechanical polishing using water (e.g. $H_2O$) to remove the release layer 106. The mechanical polishing with the water excludes a chemical slurry of abrasive particles, thereby causing no scratches to the metal layer 202 in the patterned trench 108 and causing no removal of the metal layer 202 in the patterned trench 108.

The shear force by a pad (not shown) during the mechanical polishing breaks a bond between the release layer 106 and the oxide layer 104 underneath. One skilled in the art understands the physical elements utilized in, for example, chemical mechanical polishing/planarization. These known mechanical elements are not detailed herein but are readily available to and understood by one skilled in the art.

The metal layer 202 may be a noble metal. The metal layer 202 may comprise at least one of palladium, platinum, and/or gold as well as a titanium or chromium adhesion layer between the noble metal and the oxide trench 108 surface. The substrate 102 may comprise silicon. The oxide layer 104 may be silicon dioxide. The metal layer 202 is embedded in the oxide layer 104 such that a top metal surface of the metal layer 202 is coplanar with a top oxide surface of the oxide layer 104.

In contrast the exemplary techniques of embodiments, a brief discussion is provided below to illustrate difficulties in attempting to form embedded noble metal electrodes (particularly using a palladium). It should be appreciated that standard methods in the state-of-the-art for forming a metal electrode include (1) some form of lithography to form the desired pattern in a sacrificial resist material followed by a metallization and liftoff processes, or (2) a subtractive patterning technique in which metal is blanket coated over a substrate surface followed by a resist patterning and etch process flow. In contrast to embodiments, neither of these state-of-the-art techniques are sufficient (or compatible in the latter case (2)) to create thin metal electrodes embedded in an oxide with boundaries well aligned to the oxide edges. In the former case (1), erosion of the resist sidewall from the reactive-ion etch (RIE) used to create the trenches within the oxide leads to coverage of the resist with the noble metal that is subsequently deposited to fill the trenches to create the electrodes. This scheme unfortunately makes it impossible to liftoff the metal. Multiple strategies were attempted to remove the unwanted metal and resist using standard wet chemistry techniques, resulting in either no removal or complete removal of both the unwanted material together with the (desired) metal deposited in the trenches. In contrast to state-of-the-art techniques, it was found by the inventors that shearing forces could be used to remove unwanted metal and resist in a razor blade test, using the resist as a release layer to remove the unwanted metal and resist together in accordance with embodiments.

Figure 8:
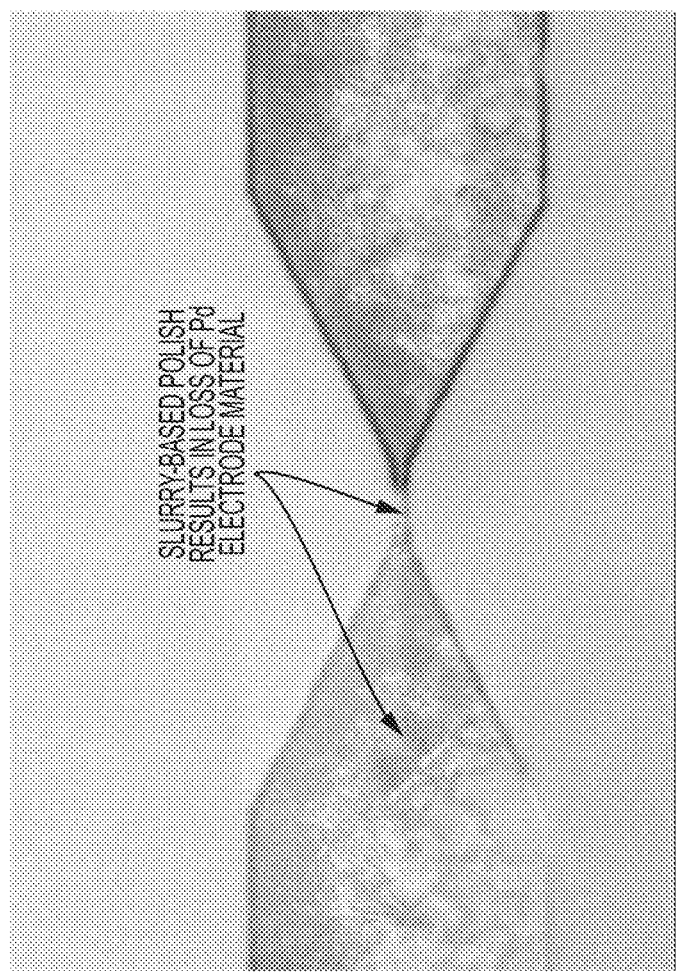
FIG. 8 is a scanning electron microscope (SEM) image illustrating attempted removal of a sacrificial resist layer utilizing a standard chemical slurry polish.

During further experiments using state-of-the-art techniques, early manufacturable chemical mechanical polish (CMP) attempts to achieve the same effect (i.e., attempting to achieve the same effect as disclosed in embodiments) using a Ceria slurry (a technique that would be used by one skilled in the art) were not successful to remove the organic planarization layer (OPL) (i.e., release layer). Complete removal of the unwanted metal in the field regions did not happen simultaneously, leaving an uneven oxide surface (which was evidenced by the spotty contrast in the oxide color), and slurry particles resulted in complete removal and/or dishing of the electrode metal in the small Pd nanowires as well as larger electrode features as shown in FIG. 8. FIG. 8 illustrates a scanning electron microscope (SEM) view of attempting to remove a sacrificial resist layer utilizing a standard chemical slurry polish. FIG. 8 shows the slurry-based polish results in loss of the palladium electrode material in the palladium electrodes and nanowire.

Figure 9:
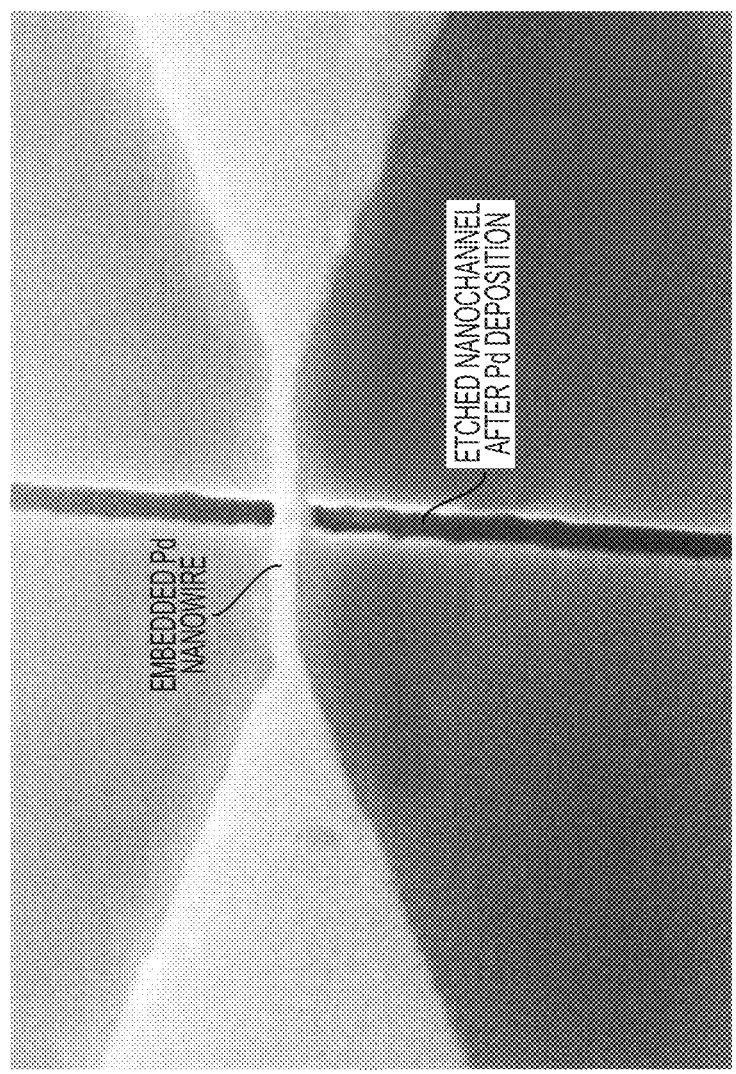
FIG. 9 is a scanning electron microscope (SEM) illustrating removal of the sacrificial resist layer utilizing a water polish according to an embodiment.

Now turning back to embodiments, in accordance with one implementation, a 60 second water polish with appropriate down force was successful in complete removal of the unwanted metal and OPL/resist stack globally across a 200 mm wafer surface while leaving the electrode features (i.e., the metal electrodes 410A and 410B) perfectly intact as shown in FIG. 9, which is a process that has been reproduced multiple times. In accordance with embodiments, the polish process also helped to minimize or remove fencing commonly associated with the release process as shown in the scanning electron microscope image in FIG. 9. FIG. 9 is a tilted scanning electron microscope (SEM) view illustrating removal of the sacrificial resist layer (i.e., release layer 106) utilizing a water polish (i.e., no slurry) according to an embodiment. Post processing of a nanochannel etched by RIE is also seen in FIG. 9. Larger electrodes can easily be separated using standard lithography when the required gap between them is greater than approximately 100 nm up to 10-100's of microns, e.g., where electrokinetic sorting of charged particles in a reservoir is needed for example (rather than using the electrodes for biomolecular detection). However, where more stringent dimensional constraints are required (e.g., the case of nanogap electrodes in a nanochannel), a He ion beam strategy can be adopted to mill the noble metal nanowire (e.g., nanowire 302) in the trench to produce a gap of tailored size down to approximately 2 nm. As discussed herein, a path for fabricating a nanogap device is disclosed which can be applied to redundant devices. In addition to nanogap devices, electrophoretic drive electrodes can also be fabricated using this technique for the purpose of separating charged particles and driving fluid flow. Such electrodes would not require nanogaps, and hence the He ion beam process can be omitted.

As discussed herein, embodiments provide noble metal electrodes that are embedded within an oxide material (for electrical isolation) with neighboring microfluidic/nanofluidic features to manipulate and detect biomolecules and other biomaterials. Embedding the metal electrodes such that the top of the electrode is coplanar with the oxide surface permits the use of sealing processes that enable medium-to high-integration of electronics on-chip, permitting a stand-alone diagnostic tool. As a stand-alone diagnostic tool, these embedded metal electrodes can be made very thin and uniform even over very large areas (several square millimeters or more) in addition to the ability to create nanoscale structures, opening up the possibility of an on-chip electrophoretic drive system for controlling fluid flow locally as well as globally. Additionally, via redundant nanogap arrangements across nanochannels made possible by this high-yield process according to embodiments, detection efficiency of nanogap electrodes can be improved through redundant measurements of single molecules in nanochannels, such as tagged or untagged bioentities.

It will be noted that various microelectronic device fabrication methods may be utilized to fabricate the components/elements discussed herein as understood by one skilled in the art. A few examples are provided below.

Deposition is any process that grows, coats, or otherwise transfers a material onto the wafer. Available technologies include physical vapor deposition (PVD), chemical vapor deposition (CVD), electrochemical deposition (ECD), molecular beam epitaxy (MBE) and more recently, atomic layer deposition (ALD) among others.

Removal is any process that removes material from the wafer: examples include etch processes (either wet or dry), and chemical-mechanical planarization (CMP), etc.

Patterning is the shaping or altering of deposited materials, and is generally referred to as lithography. For example, in conventional lithography, the wafer is coated with a chemical called a photoresist; then, a machine called a stepper focuses, aligns, and moves a mask, exposing select portions of the wafer below to short wavelength light; the exposed regions are washed away by a developer solution in the case of positive photoresist. After etching or other processing, the remaining photoresist is removed. Patterning also includes electron-beam lithography or nanoimprint lithography.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method of manufacturing a nanogap, the method comprising:
    disposing an oxide layer on top of a substrate;
    disposing a release layer in a pattern on top of the oxide layer;
    etching a patterned trench into the oxide layer using the pattern of the release layer;
    disposing a metal layer on the release layer and in the patterned trench, such that the metal layer is disposed on top of the oxide layer in the patterned trench;
    performing a polish to remove the release layer, thereby removing both the release layer and a portion of the metal layer having been disposed on top of the release layer, such that the metal layer remaining includes a first metal part and a second metal part connected by a metal nanowire, wherein the metal layer remaining is coplanar with the oxide layer;
    forming a nanochannel in the oxide layer in a region of the metal nanowire, wherein the metal nanowire intersects the nanochannel; and
    forming the nanogap in the metal nanowire, such that the first metal part and the second metal part are separated by the nanogap, the nanogap being parallel to the nanochannel and perpendicular to the metal nanowire;
    wherein the nanogap, the metal part, the second metal part, and the nanochannel lie in a same plane.

2. The method of claim 1, wherein performing the polish to remove the release layer comprises performing mechanical polishing using water to remove the release layer.

3. The method of claim 2, wherein the mechanical polishing with the water excludes a chemical slurry of abrasive particles, thereby causing no scratches to the metal layer in the patterned trench and causing no removal of the metal layer in the patterned trench.

4. The method of claim 3, wherein shear force by a pad during the mechanical polishing breaks a bond between the release layer and the oxide layer underneath.

5. The method of claim 1, further comprising forming a cover over at least the nanochannel, the nanogap, and the first and second metal parts.

6. The method of claim 1, wherein the nanogap is formed by cutting the metal nanowire to separate the first metal part and the second metal part.

7. The method of claim 1, wherein the metal layer is a noble metal.

8. The method of claim 1, wherein the metal layer comprises at least one of palladium, platinum, and gold.

9. The method of claim 1, wherein the substrate comprises silicon; and
    wherein the oxide layer is silicon dioxide.

10. The method of claim 1, wherein the metal layer is embedded in the oxide layer such that a top metal surface of the metal layer is coplanar with a top oxide surface of the oxide layer having the nanochannel.

11. The method of claim 1, further comprising after performing the polish to remove the release layer, disposing a coating of another oxide layer on top of the metal layer and the oxide layer.

12. The method of claim 1, wherein a gap size of the nanogap formed in the metal nanowire is about 2 nanometers.

* * * * *